United States Patent
Clemmer

(10) Patent No.: US 7,189,311 B2
(45) Date of Patent: Mar. 13, 2007

(54) PURIFICATION OF DIFLUOROMETHANE

(75) Inventor: Paul G. Clemmer, Williamsville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/816,529

(22) Filed: Mar. 23, 2001

(65) Prior Publication Data

US 2003/0010618 A1  Jan. 16, 2003

(51) Int. Cl.
*B01D 3/40* (2006.01)
*B01D 3/42* (2006.01)
*C07C 17/386* (2006.01)

(52) U.S. Cl. ............... 203/3; 203/67; 203/94; 203/98; 203/99; 203/DIG. 19; 570/178

(58) Field of Classification Search .......... 203/67, 203/91, 99, DIG. 19, 3, 94, 98; 570/177, 570/178
See application file for complete search history.

(56) References Cited

U.S. PATENT DOCUMENTS

| | | | |
|---|---|---|---|
| 3,101,304 A | 8/1963 | Wiist | 202/39.5 |
| 3,819,493 A | 6/1974 | Fozzard | 203/70 |
| 4,358,348 A | 11/1982 | Sulzbach | 203/67 |
| 5,087,329 A | 2/1992 | Felix | 203/67 |
| 5,200,431 A * | 4/1993 | Dattani et al. | 570/178 |
| 5,421,964 A | 6/1995 | Mahler et al. | 203/51 |
| 5,470,442 A | 11/1995 | Mahler et al. | 203/56 |
| 5,534,151 A | 7/1996 | Lee | 210/640 |
| 5,707,497 A | 1/1998 | Galland et al. | 203/75 |
| 5,763,708 A * | 6/1998 | Clemmer et al. | 570/169 |
| 5,785,822 A * | 7/1998 | Cerri et al. | 203/67 |
| 5,800,682 A * | 9/1998 | Cerri et al. | 203/99 |
| 6,156,161 A * | 12/2000 | Miller | 203/67 |
| 6,297,412 B1 * | 10/2001 | Yokoyama et al. | 570/180 |
| 6,346,172 B1 * | 2/2002 | Tsuda et al. | 203/14 |
| 6,365,580 B1 * | 4/2002 | Clemmer et al. | 514/134 |
| 6,723,887 B2 * | 4/2004 | Ramanathan et al. | 570/169 |

FOREIGN PATENT DOCUMENTS

| | | | |
|---|---|---|---|
| JP | 7291878 A | 7/1995 | |
| WO | WO 97/03936 | 2/1997 | 17/386 |
| WO | 99/07660 | * 2/1999 | |
| WO | 99/25670 | * 5/1999 | |

OTHER PUBLICATIONS

Coulson et al "Chemical Engineering" vol. 2, third ed.p. 478.*

* cited by examiner

*Primary Examiner*—Virginia Manoharan
(74) *Attorney, Agent, or Firm*—Colleen D. Szuch

(57) ABSTRACT

A method for separating difluoromethane from a mixture of difluoromethane and at least one impurity, the method involving extractively distilling the mixture using dichloromethane as an extractive agent to recover a product stream of purified difluoromethane having a concentration of impurity lower than that of the mixture.

12 Claims, 2 Drawing Sheets

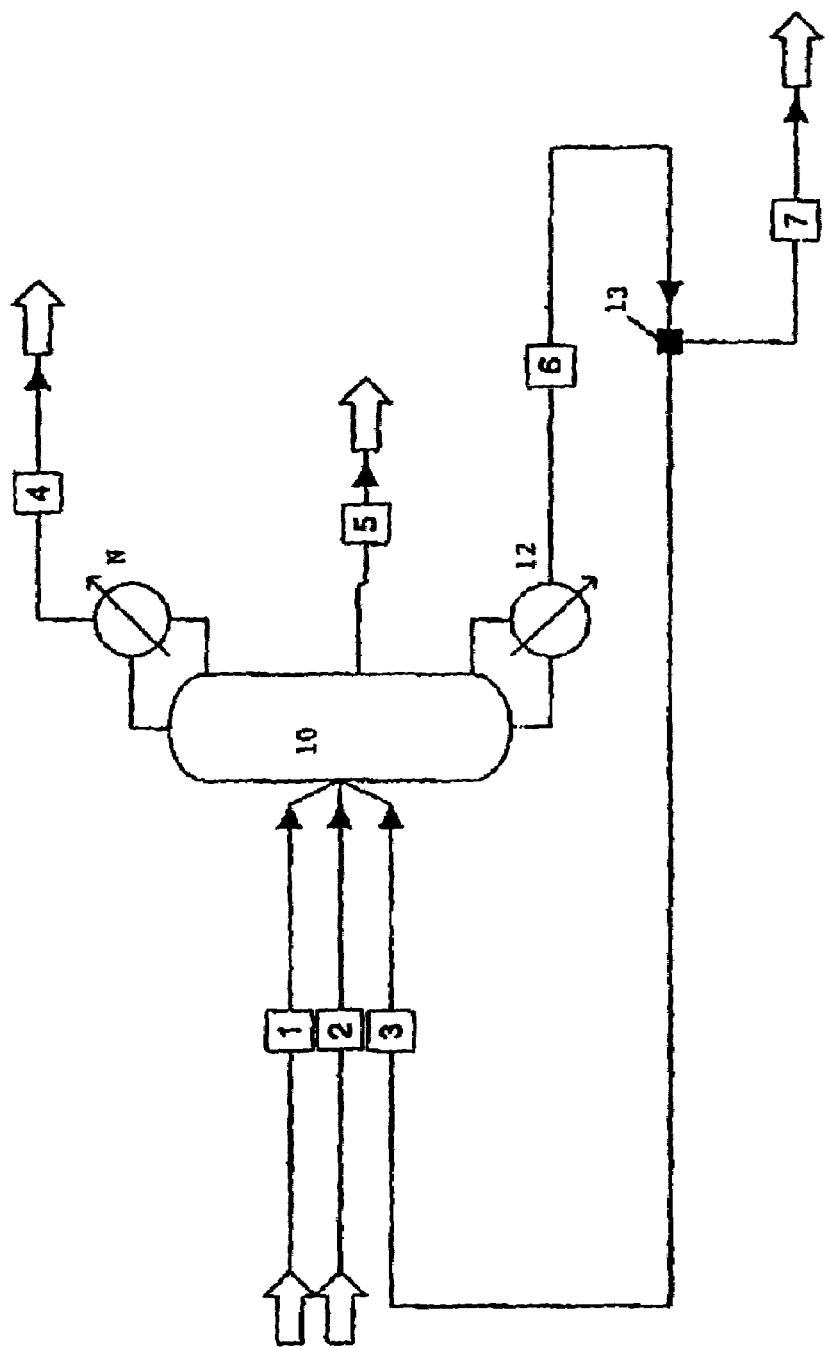
DRAWING 1

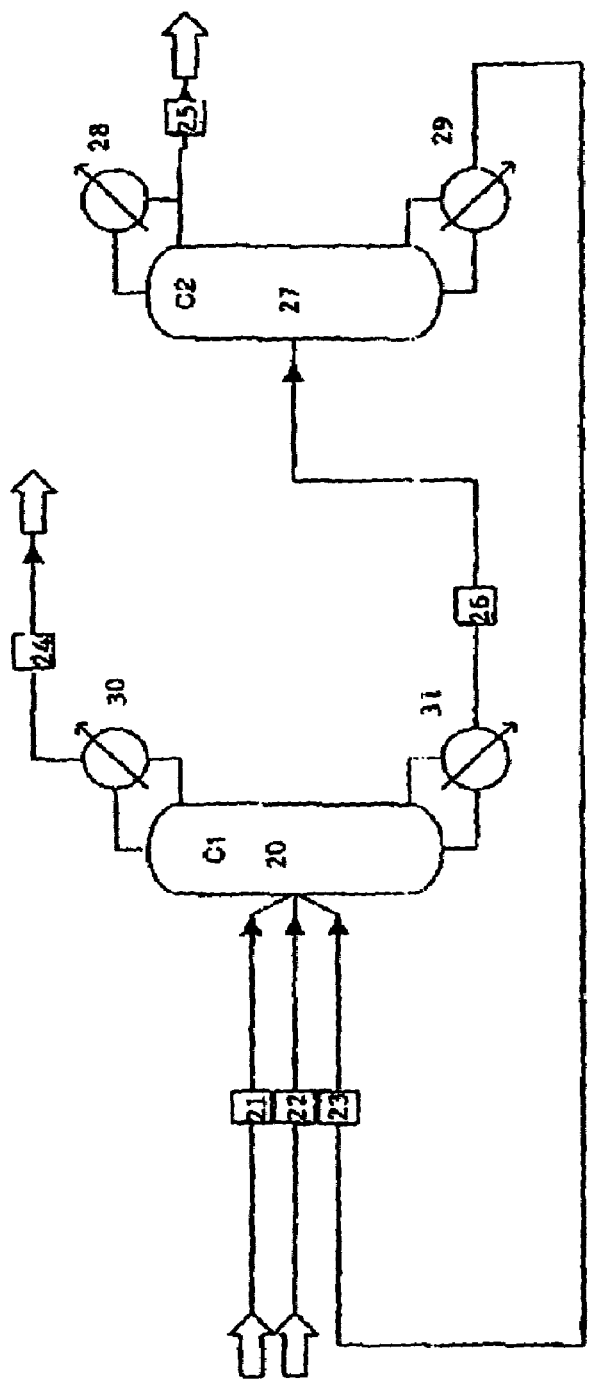
DRAWING 2

PURIFICATION OF DIFLUOROMETHANE

FIELD OF INVENTION

The present invention relates to the purification of difluoromethane (HFC-32). More specifically, this invention relates to a method and system for separating HFC-32 from an azeotropic or near-azeotropic mixture.

BACKGROUND OF THE INVENTION

Hydro fluorocarbons (HFS) have been identified as commercially-viable substitutes for chlorofluorocarbons in various applications. For example, difluoromethane (HFC-32) is useful as a refrigerant, blowing agent, cleaning agent, and aerosol propellant. Such HFS are prepared commonly by fluorinating chlorinated organic starting materials, such as dichloromethane, using a fluorination agent, such as hydrogen fluoride. Although fluorination has proved to be a convenient method for preparing HFS, particularly HFC-32, the introduction of chlorinated impurities in the product stream is generally unavoidable. Such chlorinated impurities include, for example, starting materials and intermediates from incomplete fluorination and/or by-products from undesirable side reactions. These chlorinated impurities diminish HFC-32's purity.

Although significant purification of HFC-32 can be achieved using conventional distillation, certain chlorinated impurities such as dichlorodifluoromethane (CFC-12) and methyl chloride (HCC-40) tend to form azeotropic or near-azeotropic mixtures with HFC-32 thereby rendering conventional distillation impossible or impractical. Generally, if the relative volatility of the product to the impurities in the mixture 15 is close to 1.0, conventional distillation is not practical. The relative volatility α of an impurity 2 to a fluorinated compound 1 in a mixture is defined herein according to the following equation:

$$\alpha_{2,1} = \frac{y_2}{x_2} \times \frac{x_1}{y_1}$$

where x and y are, respectively, the liquid and vapor mole fraction of the components. Therefore, for a mixture of HFC-32 and a chlorinated impurity, such as CFC-12 and/or HCC-40, where the relative volatility is close to 1.0, a separation technique other than conventional distillation is desirable.

Alternatives to conventional distillation for separating azeotropic or near-azeotropic mixtures include adsorption, membrane diffusion, and extractive distillation. Perhaps the most popular of these approaches is extractive distillation. For example, in Japanese Patent Publication No. 7-291878, an extractive distillation technique is disclosed in which an extractive agent selected from 1,1-dichloro-1-fluoroethane, 2,2-dichloro-1,1,1-fluoroethane, trichlorotrifluoroethane, and dichloropentafluoropropane is used in separate 1,1,1-trifluoroethane, pentafluoroethane or methyl chloride from HFC-32. Unfortunately, despite their effectiveness, the extractive agents described above nevertheless add impurities to the process which must be removed through additional distillation steps. These additional distillation steps add cost and complexity to the process.

Therefore, a need exists for a process of purifying HFC-32 without adding extractive agents that complicate the process and necessitate additional distillation steps. The present invention fulfills this need among others.

DESCRIPTION OF THE INVENTION AND PREFERRED EMBODIMENTS

The present invention provides both for the purification of HFC-32 through extraction distillation using dichloromethane, and for a unique fluorination/distillation configuration which avoids the need for additional distillation steps.

It has been found, surprisingly, that dichloromethane forms a non-ideal liquid-vapor mixture with HFC-32 and thus is suitable as an extraction agent in the extractive distillation of HFC-32 from a mixture of impurities. More specifically, the mixture of HFC-32 and dichloromethane exhibits non-ideal behavior according to Raoult's Law such that an increase in the concentration of dichloromethane results in a less-than-expected reduction in the mixture's volatility. Dichloromethane does not exhibit, however, the same non-ideal behavior with impurities typically found in the preparation of HFC-32. Therefore, an increase in the relative volatility between HFC-32 and the impurities can be effected by the addition of dichloromethane. The increase in relative volatility in turn provides for more effective and efficient distillation.

Accordingly, one aspect of the present invention is a method for separating difluoromethane from a mixture of the difluoromethane and at least one impurity using dichloromethane as an extractive agent. In a preferred embodiment, the method comprises extractively distilling the mixture using dichloromethane as the extractive agent to recover purified difluoromethane having a concentration of the impurity lower than that of the mixture.

Aside from forming a non-ideal mixture with HFC-32, dichloromethane is particularly advantageous as an extractive agent since it also is a starting material in the fluorination of HFC-32. Consequently, after effecting increased relative volatility between the constituents of the reactor stream and thereby facilitating extractive distillation, the dichloromethane and impurities may be removed from the distillation unit and used to feed the fluorination reaction. Thus, the need for additional distillation steps to separate the extractive agent from the impurities is eliminated.

The general concept of supplying the fluorination reaction with a mixture of the extractive agent and removed impurities is disclosed in U.S. Pat. No. 5,200,431. As disclosed therein, a bottoms stream comprising the extractive agent, trichloroethane, and impurities are fed to the fluorination reactor. Although this approach avoids the need for additional distillation steps, it makes the distillation and fluorination operations interdependent upon one another. This interdependency generally requires that the amount of extractive agent used in the extractive distillation process be no more than that consumed in the fluorination reaction. Otherwise, the extractive agent/starting material will build up in the fluorination reactor and thereby reduce productivity.

The present invention overcomes this interdependency problem by providing a novel fluorination/distillation configuration that allows for the independent operation of the fluorination and extractive distillation processes. More specifically, the extractive distillation is performed such that the extractive agent is fractionalized into a side stream and a bottoms stream. The side stream comprises a mixture of the extractive agent and impurities while the bottoms stream has a relatively-low concentration of impurities. The side stream may be supplied to the fluorination reaction. The bottoms stream may be recycled into the distillation column providing that it is sufficiently low in impurities. This configuration enables the amount of extractive agent recycled to the fluorination reaction and to the extractive distillation column to be adjusted for optimum performance. More specifically, the flow rates of the side stream and bottoms stream may be adjusted to optimize fluorination and distillation conditions. It is worthwhile to note that this configuration is not limited to HFC-32, but can be used wherever the extractive agent is also a starting material or an intermediate of the fluorinated product.

Accordingly, another aspect of the present invention is a method of preparing a fluorinated compound in which extractive distillation supplies the fluorination reaction with a controllable feed recycle stream. In a preferred embodiment, the method comprises: (a) fluorinating a chlorinated organic compound to produce a reactor stream comprising a fluorinated compound and at least one chlorinated impurity; (b) feeding the mixture to a distillation unit; (c) feeding an extractive agent to the distillation unit, wherein the extractive agent is the chlorinated organic compound; (d) operating the distillation unit under conditions sufficient to distill a product stream of the fluorinated compound containing a concentration of the impurity less than that of the reactor stream; (e) withdrawing a side stream from the distillation unit, the side stream comprising the impurity and the extractive agent; (f) withdrawing a bottom stream from the distillation unit, the bottom stream comprising the extractive agent and having a concentration of impurity less than that found in the side stream; (g) supplying the fluorination reaction with at least a portion of the side stream; and (h) recycling at least a portion of the bottom stream into the distillation unit.

Yet another aspect of the invention is a system for preparing a fluorinated compound which provides for independent recycle streams to the fluorination and distillation operations. In a preferred embodiment, the method comprises: (a) a reactor adapted to receive a chlorinated organic compound from at least one source and a fluorination agent for fluorinating the chlorinated organic compound, the reactor adapted to facilitate fluorination of the chlorinated organic compound to produce a reactor stream comprising a mixture of a fluorinated compound and at least one chlorinated impurity; (b) a first conduit for feeding the reactor stream to a distillation unit; (c) a distillation unit configured to receive the mixture and an extraction agent from at least one source, the distillation unit being adapted to facilitate extractive distillation of the mixture to produce an overheads stream, a side stream, and a bottoms stream, the overheads stream comprising the fluorinated compound and a lower concentration of chlorinated impurities than that of the reactor stream, the side stream comprising the extractive agent and the chlorinated impurity, the bottoms stream comprising the extractive agent and a concentration of the chlorinated impurity less than that of the side stream; (d) a second conduit for supplying at least a portion of the side stream to the fluorination reactor; and (e) a third conduit for recycling at least a portion of the bottoms stream to the distillation unit.

Considering now the purification of HFC-32 in particular, the invention may be applied to any mixture of HFC-32 and one or more impurities having a volatility above that of dichloromethane. The purification method is especially applicable to mixtures obtained in the preparation of HFC-32 through the fluorination of chlorinated organic compounds. Such mixtures usually comprise HFC-32, hydrogen fluoride, and at least one chlorinated impurity (usually a starting material, intermediate, or unwanted byproduct) having the formula:

$$CH_wCl_yX_z$$

wherein each X is an independently selected halogen, $y \geq 1$ and $w+y+z=4$. Typically, X is fluorine. For example, chlorinated impurities typically found in a reactor stream of HFC-32 include chlorofluoromethane (HCFC-31), chloromethane (HCC-40), dichloromethane (HCC-30), chlorodifluoromethane (HCFC-22), chlorotrifluoromethane (CFC-13), dichlorodifluoromethane (CFC-12) and combinations of two or more thereof. The method is particularly appropriate for azeotropic or near-azeotropic mixtures, such as mixtures of HFC-32 and CFC-12 and/or HCC-40. It is worthwhile to note, however, that the method is not restricted to azeotropic or near-azeotropic mixtures and can improve the distillation of various mixtures by increasing the relative volatility between the constituents.

The concentration of the chlorinated impurity in the reactor stream being treated in accordance with the invention is typically from 20 to 5000 ppm by weight, but mixtures containing smaller or larger amounts of the chlorinated impurity also may be separated.

The method of the invention may be performed using conventional extractive distillation procedures. Generally, it is preferable to conduct the extractive distillation near or above atmospheric pressure to minimize operation costs. For example, suitable results have been obtained operating at a pressure of about 1 to about 15 bars. The temperature at which the distillation unit is operated depends upon the operating pressure. It is particularly advantageous that dichloromethane is both an extractive agent and a starting material in the preparation of HFC-32. This way, the bottoms fraction from the extractive distillation unit comprising dichloromethane and other chlorinated species can be supplied to the fluorination reaction. In a preferred embodiment of the present invention, rather than feeding the bottoms fraction to the fluorination reaction, a configuration is used which fractionalizes the extractive agent into two streams: a side stream comprising extractive agent mixed with impurities and a bottoms stream comprising extractive agent and having a low concentration impurity. The bottoms stream preferably has no greater than about 5000 ppm (by weight) impurities, and, more preferably, no greater than about 1000 ppm. The side stream is supplied to the fluorination reaction and the bottoms stream is recycled to the distillation unit. Thus, the amount of feed supplied to the fluorination reactor can be reduced by increasing the amount of the bottoms stream recycled to the distillation unit and vice versa.

If desired, the reactor stream may be pre-treated to effect partial or essentially complete removal of one or more other chlorinated impurities and/or hydrogen fluoride before performing the separation method of the present invention. Such a pretreatment step is preferable where the relative volatility of the product and an impurity is greater than about 1.1 such that conventional distillation is readily achieved without the use of a particularly tall distillation column. Furthermore, some form of pretreatment may be preferred if the impurity has a lower volatility than dichloromethane in which case combining it with dichloromethane would diminish the relative volatility of the mixture.

The distillation preferably is conducted to effect a distillation stream of purified HFC-32 having less than about 50 ppm (by weight) chlorinated impurities. More preferably, the reaction is conducted to effect a distillation stream having less than about 10 ppm chlorinated impurities. Furthermore, in accordance with the present invention, high yields of HFC-32 are realized. In a preferred embodiment, the yield of HFC-32 is no less than about 80% and, more preferably, no less than about 90%.

Referring now to the drawings, two preferred embodiments of the system are schematically illustrated. In FIG. 1, a distillation column 10 is shown having feed lines 1 and 2 connected to its center portion. An overheads flow line 4a leads from the top of the column 10 to a condenser 11. A product flow line 4 leads from the top of the condenser 32 while a reflux flow line 4b leads from the bottom of the condenser back to the distillation column 10. A side flow line 5 leads from the center portion of the column 10 to a fluorination reactor (not shown). A bottoms flow line 6a leads from the bottom of the column 1 to a reboiler 12 with a vapor return line 6b leading from the top of the reboiler back to the bottom of the column 10. A flow line 6 leads from the bottom of the reboiler 12 and is fed to the center portion of the column 10 as recycle feed line 3. A diversion valve 13 is disposed along flow line 6 to divert a desired portion of the flow to flow line 7 which optionally connects to a fluorination reactor (not shown).

In operation, an impure reactor stream containing a fluorinated compound, such as HFC-32, and one or more chlorinated impurities is fed into a distillation column 10 through feed line 1 along with an extractive agent, for example, dichloromethane, through feed line 2. Optionally, a recycle stream also may be fed to the column via the recycle feed line 3. The distillation column 10 is operated at conditions and with reflux ratios sufficient to effect distillation of a purified fluorinated compound through a product stream in the product flow line 4. The product stream comprises the fluorinated compound and a concentration of impurity less than that of the reactor stream. Removal of impurities from the distillation unit 10 is effected through a side stream through side flow line 5. The side stream optionally may be fed to the fluorination reactor (not shown). The bottoms stream leaving through the bottoms flow line 6 is rich in extractive agent and has a concentration of impurities less than that of the side stream. Optionally, it may be recycled back to the distillation column 10.

The location of the feed points, temperature and relative flow rates of the feed streams, reflux ratios, column size and distillation operating parameters are adjusted to optimize the process operation to achieve the desired separation. Furthermore, although the use of this configuration has been described with respect to dichloromethane, this configuration can be practiced wherever the extractive agent is a starting material or intermediate of the fluorination reaction.

According to this configuration, the distillation unit not only provides for the separation of the impurity from the product, but also provides for the separation of extractive agent from a mixture of extractive agent and one or more impurities. This way, the impurities are removed from the distillation unit but a recycle stream is still available.

In FIG. 2, an alternative distillation system is shown schematically. A distillation column 20 is shown with a feed line 21, an extractive agent feed line 22, and a recycle feed line 23 connected to its center portion. An overheads flow line 24a leads from the top of the column 20 to a condenser 30. A product flow line 24a leads from the top of condenser 30 while reflux flow line 24b leads from the bottom of the condenser 30 back to the top of the column 20. A bottoms flow line 26a leads from the bottom of the column 20 to a reboiler 31. A vapor return line 26b leads from the top of the reboiler back to the bottom of the column 20 and a flow line 26 leads from the reboiler 31 to a second distillation column 27. An overheads flow line 25a leads from the top of the column 27 to a condenser 28. An impurity flow line 25 leads from the top of condenser 28. A reflux flow line 25b leads from the impurity flow line 25 back to the top of the column 20. A bottoms flow line 23a leads from the bottom of the column 27 to a reboiler 29. A vapor return line 23b leads from the top of the reboiler 29 back to the bottom of the column, while an extractive agent flow line 23 leads from the bottom of the reboiler 29 and optionally feeds the distillation column 20.

In operation, the impure reactor stream is fed through feed line 21 and the extractive agent, for example, dichloromethane is fed through the feed line 22 to the first distillation column 20. Optionally, a recycle stream also may be fed to the first distillation column through recycle feed line 23. The distillation column 20 is operated at conditions sufficient to effect distillation of a purified fluorinated compound, such as HFC-32, through a product stream in the product flow line 24. Removal of impurities and extractive agent is effected through a bottoms stream in line 26. This bottoms stream then is fed to the second distillation unit 27. Impurities are removed as distillate in an impurities stream through line 25, while extractive agent is removed in a bottoms stream through line 23. The bottoms stream, rich in extractive agent, optionally may be recycled to the first distillation unit 20. Again, the location of the feed points, temperature and relative flow rates of the feed streams, column size and distillation operating parameters are adjusted to optimize the process operation to achieve the desired separation.

In both configurations described above, to lower operating costs, all columns in the scheme preferably operate at near- or super-atmospheric pressure. The recycle streams preferably are cooled before being fed to the distillation units. Furthermore, the product obtained by the method of the invention may be subjected, as desired, to further purification procedures.

BRIEF DESCRIPTION OF DRAWINGS

FIG. 1 shows a preferred embodiment of the invention in which a distillation column comprises a side stream feed for a fluorination reactor.

FIG. 2 shows an alternative embodiment of the invention in which the bottoms of a distillation column feed a fluorination reactor.

COMPARATIVE EXAMPLE

A sample of impure HFC-32 produced by fluorination of dichloromethane was fed to a stainless steel distillation column with approximately 40 theoretical stages equipped with a reboiler and condenser, operating at a pressure of approximately 11.5 bar. Table 1 gives the amount of several impurities as a ratio to the HFC-32 content, as measured in the feed and at the top and bottom of the distillation column. The results demonstrate that the impurities were not effectively removed by conventional distillation.

TABLE 1

| Impurity | Feed liquid (wt %) | Distillate (wt %) | Reboiler vapor (wt %) |
|---|---|---|---|
| Methyl chloride | 0.0039 | 0.0010 | 0.0060 |
| Dichlorofluoro- | 0.1430 | 0.0436 | 0.1659 |

TABLE 1-continued

| Impurity | Feed liquid (wt %) | Distillate (wt %) | Reboiler vapor (wt %) |
|---|---|---|---|
| methane | | | |
| Dichlorodifluoro-methane | 0.0876 | 0.1626 | 0.0232 |
| Chlorofluoro-methane | 0.6923 | 0.0003 | 1.04 |

EXAMPLE 1

The feed impure HFC-32 was continued at approximately the same distillation conditions as the comparative example to test the feasibility of removing impurities from HFC-32 by extractive distillation using dichloromethane as the extractive agent. Dichloromethane was fed to the column at a location above the HFC-32 feed point at a mass feed rate 6.5 times that of the HFC-32 feed. Table 2 gives the amount of several impurities as a ratio to the HFC-32 content, as measured in the feed and at the top and bottom of the distillation column while doing this extractive distillation. These results demonstrate that dichloromethane is an effective extractive agent for removing the listed impurities from HFC-32 by extractive distillation.

TABLE 2

| Component | Feed liquid (wt %) | Distillate (wt %) | Reboiler vapor (wt %) |
|---|---|---|---|
| Methyl chloride | 0.0039 | 0.0002 | 0.0111 |
| Dichlorofluoro-methane | 0.1430 | 0.0146 | 0.3660 |
| Dichlorodifluoro-methane | 0.0876 | 0.0053 | 0.0870 |
| Chlorofluoro-methane | 0.6923 | 0.0002 | 1.342 |

What is claimed is:

1. Method for separating difluoromethane from a mixture of difluoromethane and at least one impurity, said method comprising the steps of:
   extractively distilling said mixture using dichloromethane as an extractive agent to produce an overhead stream of purified difluoromethane having a concentration of said at least one impurity lower than that of said mixture, and a side stream and a bottoms stream, said side stream comprising a mixture of dichloromethane and said at least one impurity, said bottoms stream comprising dichloromethane and a concentration of said at least one impurity having a concentration less than that of said side stream; and
   supplying at least a portion of said side stream to a fluorination reaction which produces said mixture.

2. The method of claim 1, wherein said at least one impurity is a chlorinated impurity having the formula:

$CH_wCl_yX_z$ wherein each X is an independently selected halogen, y≧1 and w+y+z=4.

3. The method of claim 2, wherein X is fluorine.

4. The method of claim 2, wherein said chlorinated impurity is selected from the group consisting of chlorofluoromethane, chloromethane, chlorodifluoromethane, dichlorodifluoromethane and combinations of two or more thereof.

5. The method of claim 4, wherein said chlorinated impurity is selected from the group consisting of dichlorodifluoromethane, chloromethane and combinations thereof.

6. The method of claim 1, wherein the concentration of said at least one impurity in the purified difluoromethane is no greater than about 50 ppm by weight.

7. The method of claim 6, wherein the concentration of said at least one impurity in said purified difluoromethane is no greater than about 10 ppm.

8. The method of claim 1, wherein the yield of said purified difluoromethane is no less than about 80%.

9. The method of claim 1, wherein the step of extractively distilling is conducted at a pressure of about 1 to about 15 bars.

10. A method for purifying difluoromethane comprising the steps of:
    fluorinating a dichloromethane to produce a reactor stream comprising a mixture of difluoromethane and at least one impurity;
    feeding said mixture to a distillation unit;
    feeding an extractive agent to said distillation unit, wherein said extractive agent is said dichloromethane;
    operating said distillation unit under conditions sufficient to distill a product stream comprising said difluoromethane and a concentration of said at least one impurity less than that of said reactor stream;
    withdrawing a side stream from said distillation unit, said side stream comprising said impurity and said extractive agent;
    withdrawing a bottoms stream from said distillation unit, said bottoms stream comprising said extractive agent and a concentration of said impurity less than that of said side stream;
    supplying the fluorination reaction with at least a portion of said side stream; and
    recycling at least a portion of said bottoms stream to said distillation unit.

11. The method of claim 10 wherein the step of extractively distilling is conducted at a pressure of about 1 to 15 bars.

12. A system for the preparation of a fluorinated compound comprising:
    a fluorination reactor connected to a source of dichloromethane, a source of fluorine, and a source of recycled dichloromethane from a distillation unit to facilitate fluorination of dichloromethane and to produce a reactor stream comprising a mixture of a fluorinated compound and an impurity;
    a first conduit for feeding said mixture to a distillation unit;
    a distillation unit connected to said first conduit and to a source of dichloromethane for extractive distillation of said mixture to produce an overheads stream, a side stream, and a bottoms stream;
    a second conduit for supplying at least a portion of a side stream to said fluorination reactor;
    a third conduit for recycling at least a portion of said bottoms stream to said distillation unit; and
    a valve connected to said third conduit for diverting a portion of the bottoms stream from said distillation unit to said fluorination reactor.

* * * * *